United States Patent [19]

Blosser et al.

[11] Patent Number: 4,641,104
[45] Date of Patent: Feb. 3, 1987

[54] SUPERCONDUCTING MEDICAL CYCLOTRON

[75] Inventors: Henry G. Blosser, East Lansing, Mich.; Richard J. Burleigh, Berkeley, Calif.; Gabe F. Blosser, Haslett; Emanuel B. Jemison, Kalamazoo, both of Mich.

[73] Assignee: Board of Trustees operating Michigan State University, East Lansing, Mich.

[21] Appl. No.: 604,089

[22] Filed: Apr. 26, 1984

[51] Int. Cl.$^4$ ............................................. H05H 13/00
[52] U.S. Cl. ....................................... 328/234; 313/62; 250/493.1; 335/216; 376/112
[58] Field of Search .................... 328/234; 313/35, 62; 250/492.1, 497.1, 498.1, 493.1; 165/58, 60; 174/15 R, 15 CA, 15 S; 335/216; 376/112

[56] References Cited

U.S. PATENT DOCUMENTS

| | | | |
|---|---|---|---|
| 3,868,522 | 2/1975 | Bigham et al. | 313/62 |
| 3,925,676 | 12/1975 | Bigham et al. | 376/112 |
| 4,112,306 | 9/1978 | Nunan | 250/499 |
| 4,507,616 | 3/1985 | Blosser et al. | 313/62 X |

OTHER PUBLICATIONS

Hepburn et al., Int. J. Radiation Oncology, 3, 387–391, (1977).

Primary Examiner—David K. Moore
Assistant Examiner—K. Wieder
Attorney, Agent, or Firm—Ian C. McLeod

[57] ABSTRACT

An improved superconducting cyclotron (10) particularly useful for medical or therapeutic purposes is described. The vessel (105) for liquified gas surrounding superconducting coils (101, 101a) is provided with a capillary tube (200) joined to a semi-circular tube (123) leading into an exit tube (201) from the vessel which provides Joule-Thompson effect cooling upon flow of a portion of the liquified gas in the vessel into the semi-circular tube. The cooling maintains the liquified gas in the vessel in a subcooled condition to prevent boiling. The liquified gas from the exit tube can be used to cool the magnetic poles (103, 104) and then can be vented to the atmosphere or recycled. A special external magnetic yoke (102) configuration for weight reduction is described. Also described is a flexible hose (37) for supplying the liquified gas to and from the cyclotron which is mounted in a helical coil so as to allow up to a 360° of rotation of the cyclotron. Finally a movable floor (27) around the cyclotron is described.

21 Claims, 18 Drawing Figures

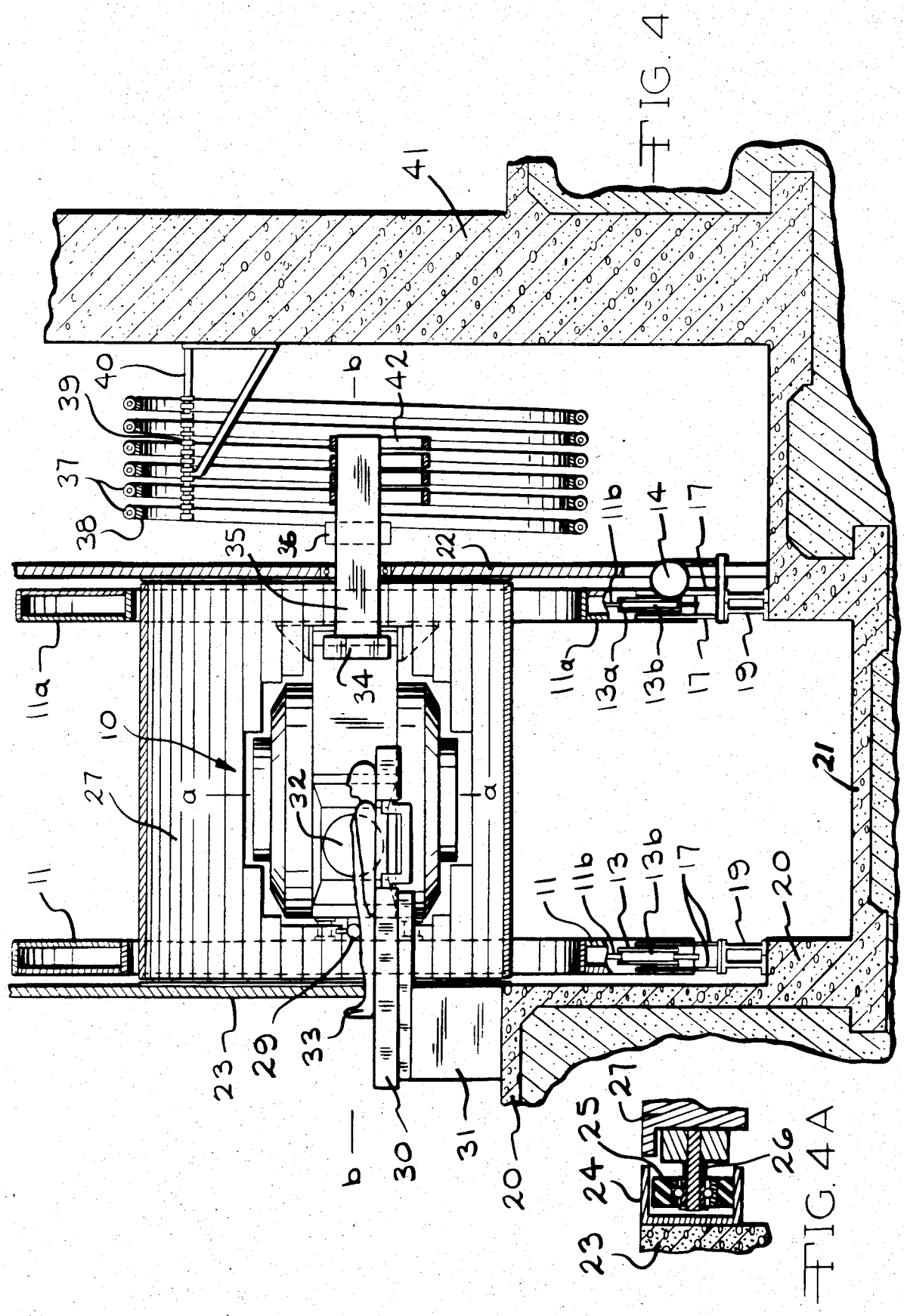

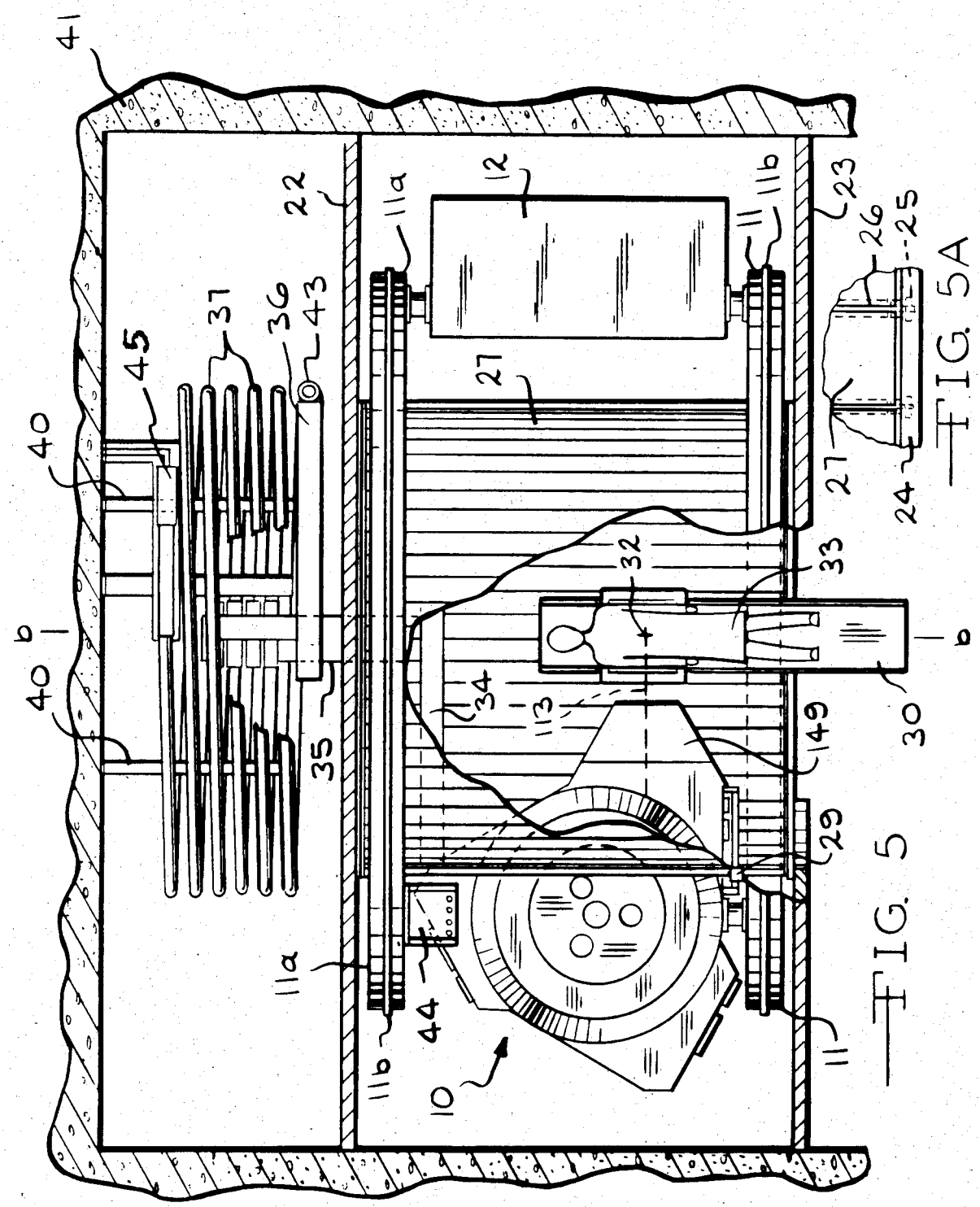

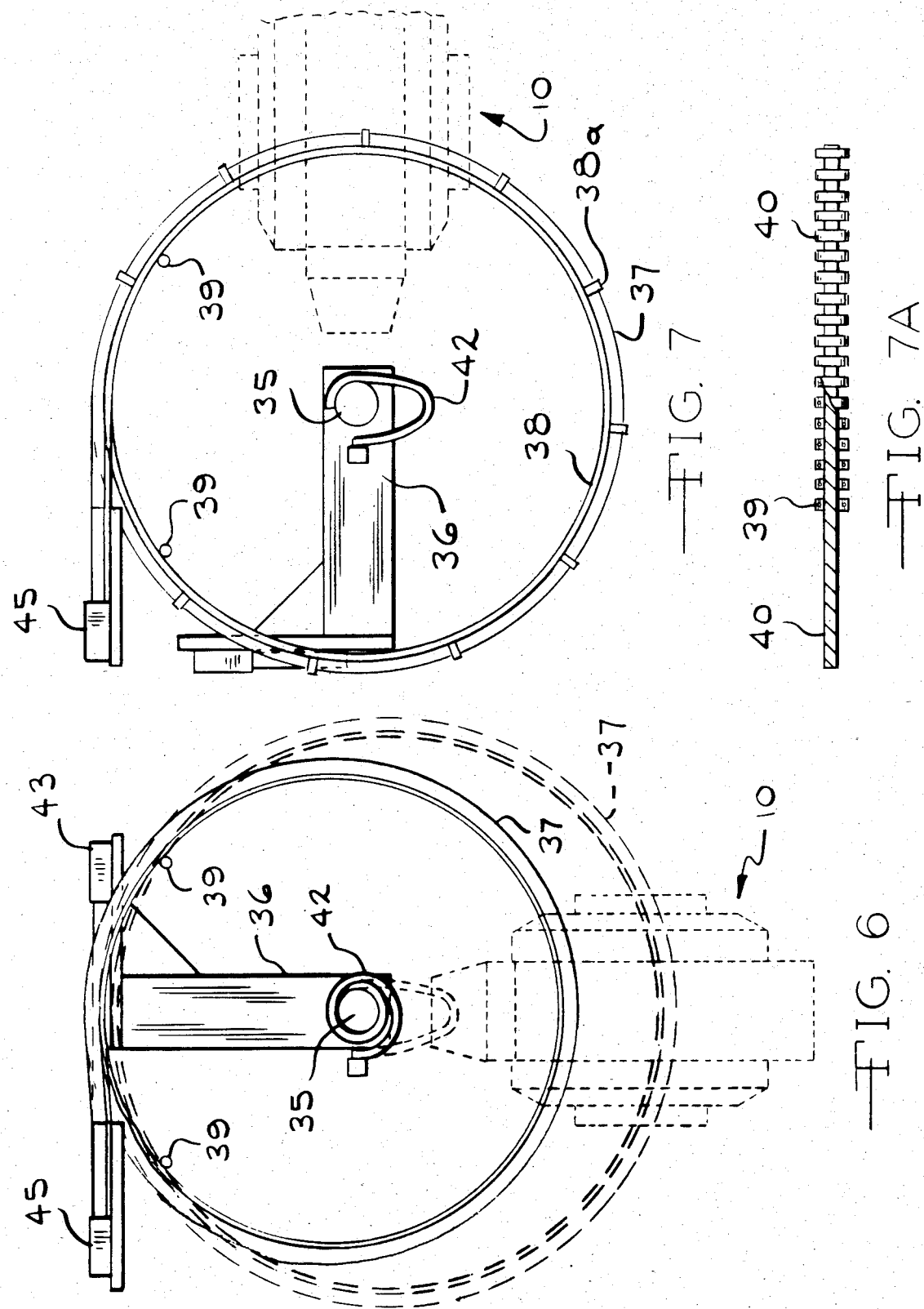

SUPERCONDUCTING MEDICAL CYCLOTRON

BACKGROUND OF THE INVENTION

The present invention relates to superconducting cyclotrons (10), particularly movable cyclotrons useful for therapeutic purposes. In particular the present invention relates to a rotatable superconducting cyclotron with a unique supplementary cooling system for a vessel (105) surrounding superconducting coils (101, 101a) which prevents localized boiling of the liquified gas adjacent the coils.

PRIOR ART

The prior art shows various types of cyclotrons some of which are superconducting. U.S. Pat. No. 3,868,522 describes a superconducting cyclotron. Other prior art shows medical or therapeutic cyclotrons. Such prior art includes Hepburn et al., Int. J. Radiation Oncology 3 387-391 (1977) and U.S. Pat. No. 3,925,676 which show a cyclotron which is mounted around a patient on a counterweight balanced bar and is rotatable on a pivot means on the bar. Another rotatable cyclotron is described in U.S. application Ser. No. 355,337 filed Mar. 8, 1982, now U.S. Pat. No. 4,507,616 which includes some of the inventors herein. The improvement in U.S. Pat. No. 4,507,616 relates to a cyclotron which is rotatable in an arc of only 180° around the patient so that the liquified gas in the coil cooling vessel, which can boil, can be vented to the atmosphere and thus the coils are covered with the liquified gas only part of the time. The problem with this construction is that the coils can possibly overheat locally. Further up to 360° of rotation of the cyclotron is desirable for patient treatment but is not possible with the cyclotron of U.S. Pat. No. 4,507,616.

Presently the technology has not been available for 360° rotation of a superconducting cyclotron, conventional pool boiling cooling systems being not compatible with rotation of the cooling vessel into an upside down position. U.S. Pat. No. 4,112,306 shows a non-superconducting cyclotron which is rotatable on a large hollow bearing such that the patient passes through the bearing. The large size of the bearing makes this a costly design. Further when the counterweight is mounted in a "diametrically opposed" relation to the cyclotron, as described in Claims 4 and 5 of this patent, the lateral moment which must be resisted by both the bearing and wall are exceedingly large, leading to prohibitively expensive structures. The double ring support system described in the present application hereinafter allows the counterweight to be positioned in a diametrically opposed relation to the cyclotron so that the counterweight functions as a neutron beam stop or absorber and at the same time the whole structure is balanced and can therefore mount on inexpensive wheels with small inexpensive bearings.

The reduced weight of the superconducting cyclotron as compared with a room temperature cyclotron allows the use of deuterons as the accelerated particle, which is desirable since deuterons have been the particle most used in previous radiation therapy tests and results in reduced radioactivity in the target as compared with the proton target system described in U.S. Pat. No. 4,112,306. A superconducting cyclotron of reduced weight which reduces the load on the support structure for rotating the cyclotron and yet is adequately shielded is needed. These needs then dictated a superconducting cyclotron which was functionally different from that of U.S. Pat. No. 4,507,616 and the others shown in the prior art.

OBJECTS

It is therefore an object of the present invention to provide a superconducting cyclotron which can rotate up to 360° around a patient or other object. Further still, it is an object of the present invention to provide a superconducting cyclotron which has a unique configuration for an iron yoke around the magnetic poles and coils which significantly increases the convenience and reduces the cost of mounting auxiliary equipment on the yoke. Further still it is an object of the present invention to provide a therapeutic superconducting medical cyclotron system which is relatively inexpensive and simple to construct and operate. Further still, it is an object of the present invention to provide effective means for supplying liquified gas and electricity to the cyclotron system as it rotates. Finally it is an object of the present invention to provide a floor system as part of the cyclotron system which gives medical technicians and doctors good access to the patient without the complexity and expense of independently driven floor systems which have been previously employed in prior art cyclotron systems. These and other objects will become increasingly apparent by reference to the following description and to the drawings.

IN THE DRAWINGS

FIG. 2A shows the details of one retaining member (137).

Figure 1:
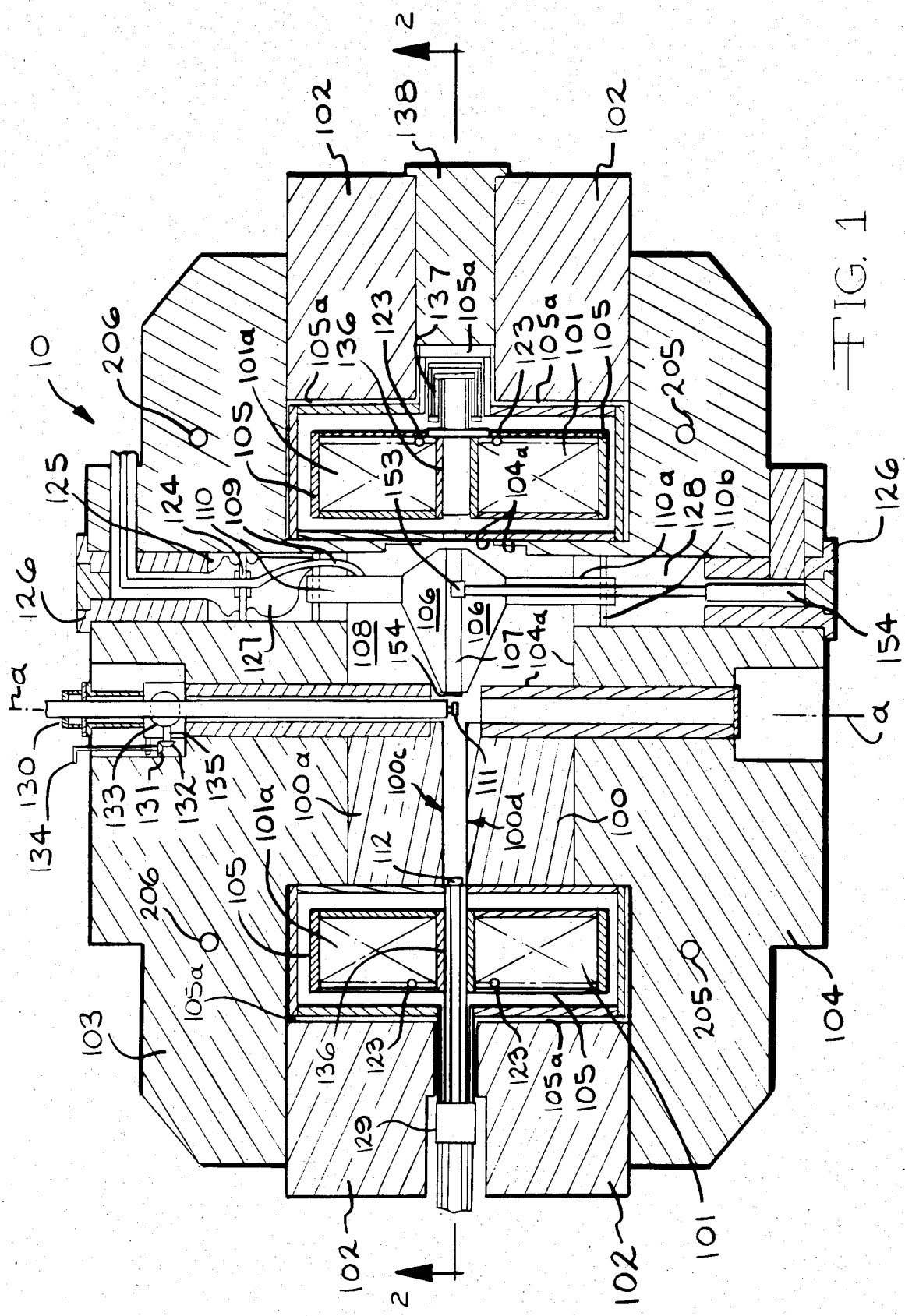
FIG. 1 is a front cross-sectional view of a cyclotron (10), particularly illustrating a vessel (105) for housing superconducting coils (101, 101a) around poles (100, 100a) and also the position and construction of retaining members (137) in the form of a folded column for holding the coils in position.
Figure 2:
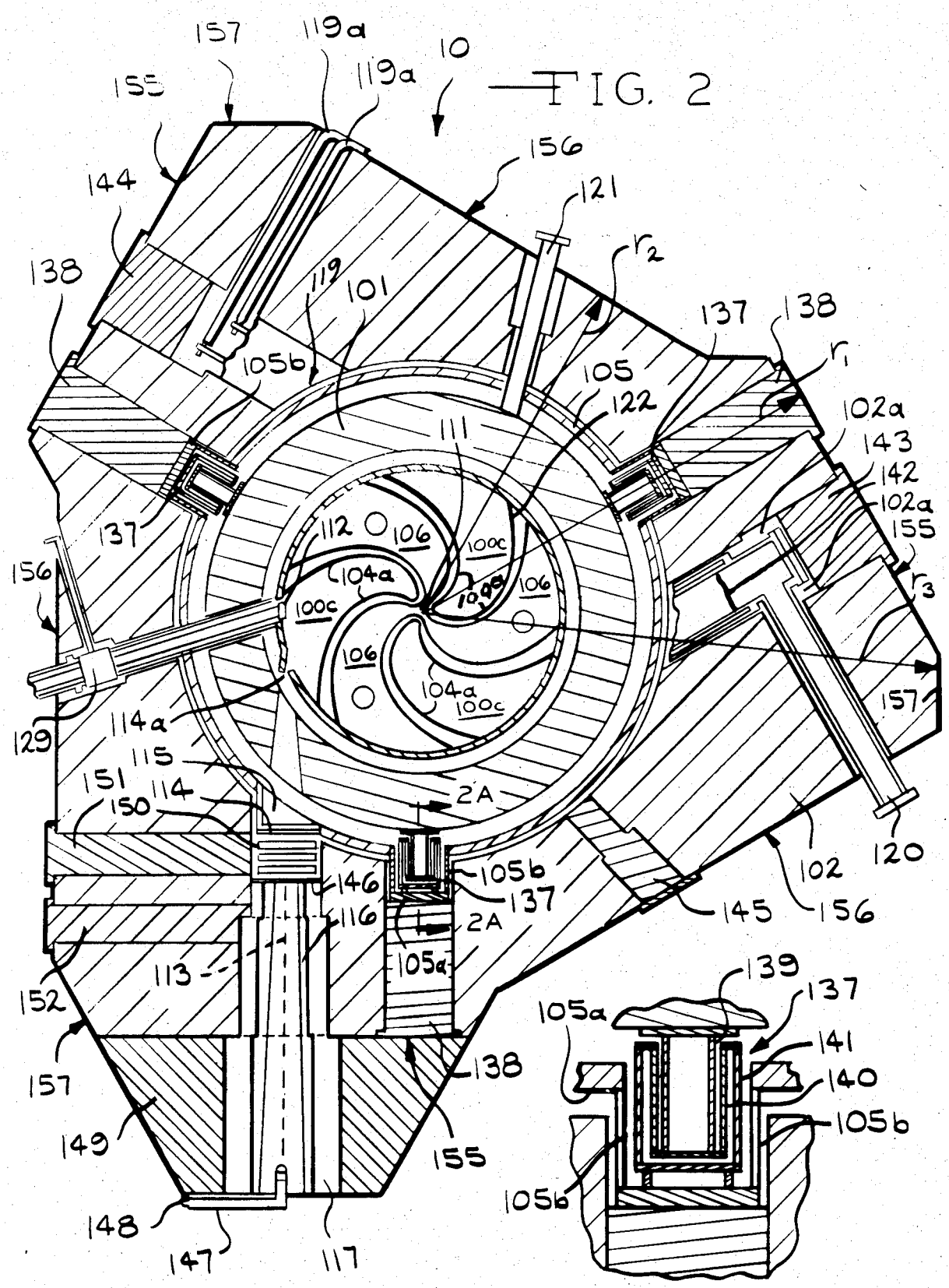
FIG. 2 is a plan cross-sectional view of the cyclotron (10) of FIG. 1 along line 2—2 particularly illustrating a unique yoke (102) cross-section with multiple flat faces (155,156) for connection of components to the center of the cyclotron.

FIG. 4 is a front cross-sectional view of a preferred therapy cyclotron (10), particularly illustrating dual spaced parallel rings (11, 11a), supporting the cyclotron (10) of FIGS. 1 and 2 between them, which are supported by rollers (13, 13a) and further illustrating helically coiled flexible hose (37) for supplying liquified gas to and from the cyclotron in the vessel (105) around the coils (101, 101a) as it rotates.

FIG. 4a is an enlarged partial section front view of a portion FIG. 4 showing rollers (25) in a track (24) supporting slats (27) providing a movable floor.

FIG. 5 is a plan view of the therapy cyclotron (10) shown in FIG. 4 particularly illustrating the mounting of the cyclotron and counterweight (12).

FIG. 5a is an enlarged partial section plan view of a portion of FIG. 5 illustrating a section of slats (27) of the movable floor of FIGS. 4 and 4a.

FIGS. 6 and 7 are right end views of the cyclotron (10) of FIG. 4, particularly illustrating the helically coiled flexible hose (37) for the liquified gas and supporting springs (38) with holding clips (38a) as well as a centrally located drum (35) for supporting the electrical cable (42) to the cyclotron as it rotates.

FIG. 7A shows details of the rollers (39) which 1 support the hose (37).

Figure 8:
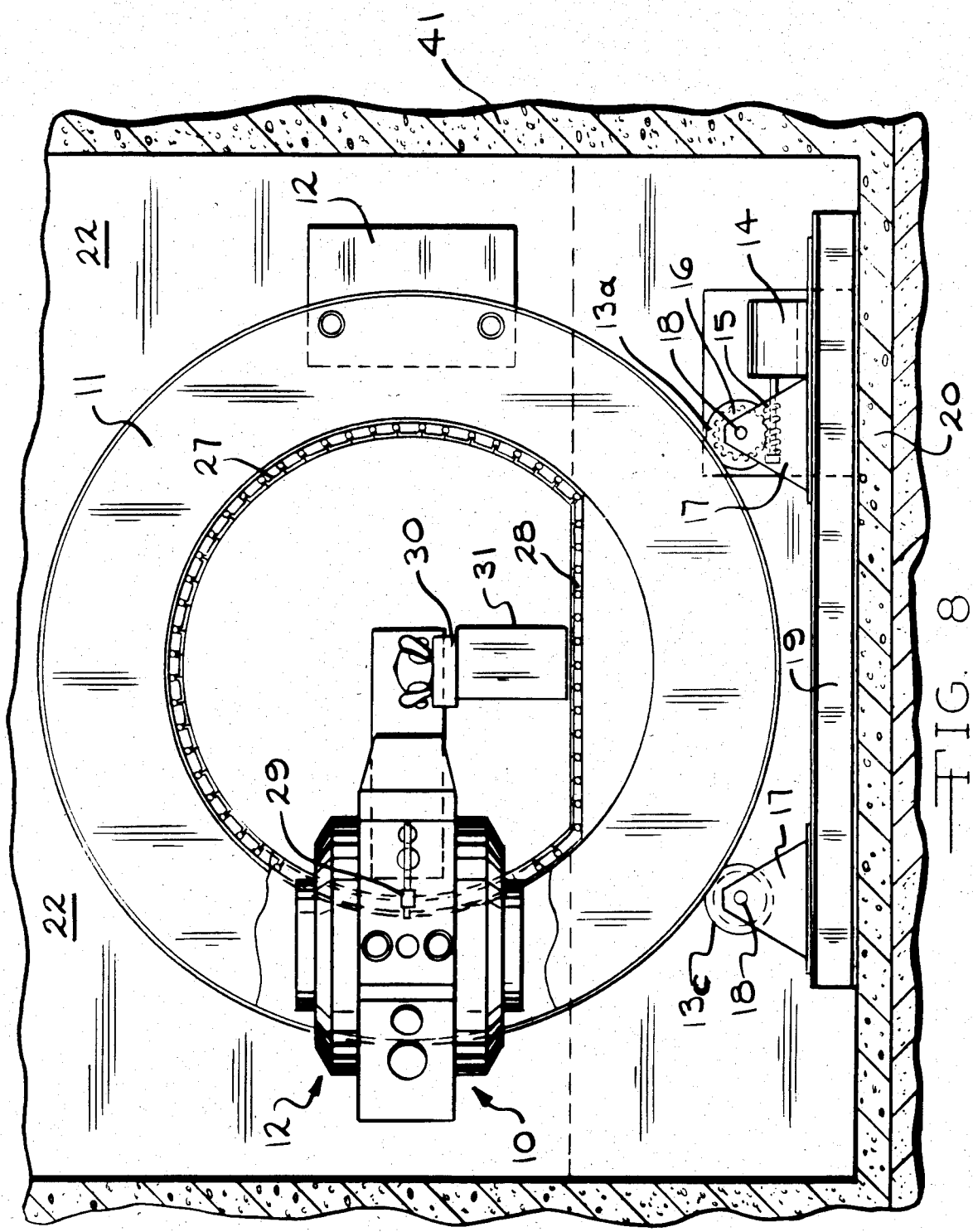

FIG. 8 is a left end view of the cyclotron (10) shown in FIG. 4, particularly illustrating the mounting of the cyclotron (10) and counterweight (12), the slats (27) of the movable floor and the rollers (13, 13b) supporting the cyclotron on rings (11 and 11a).

Figure 9:
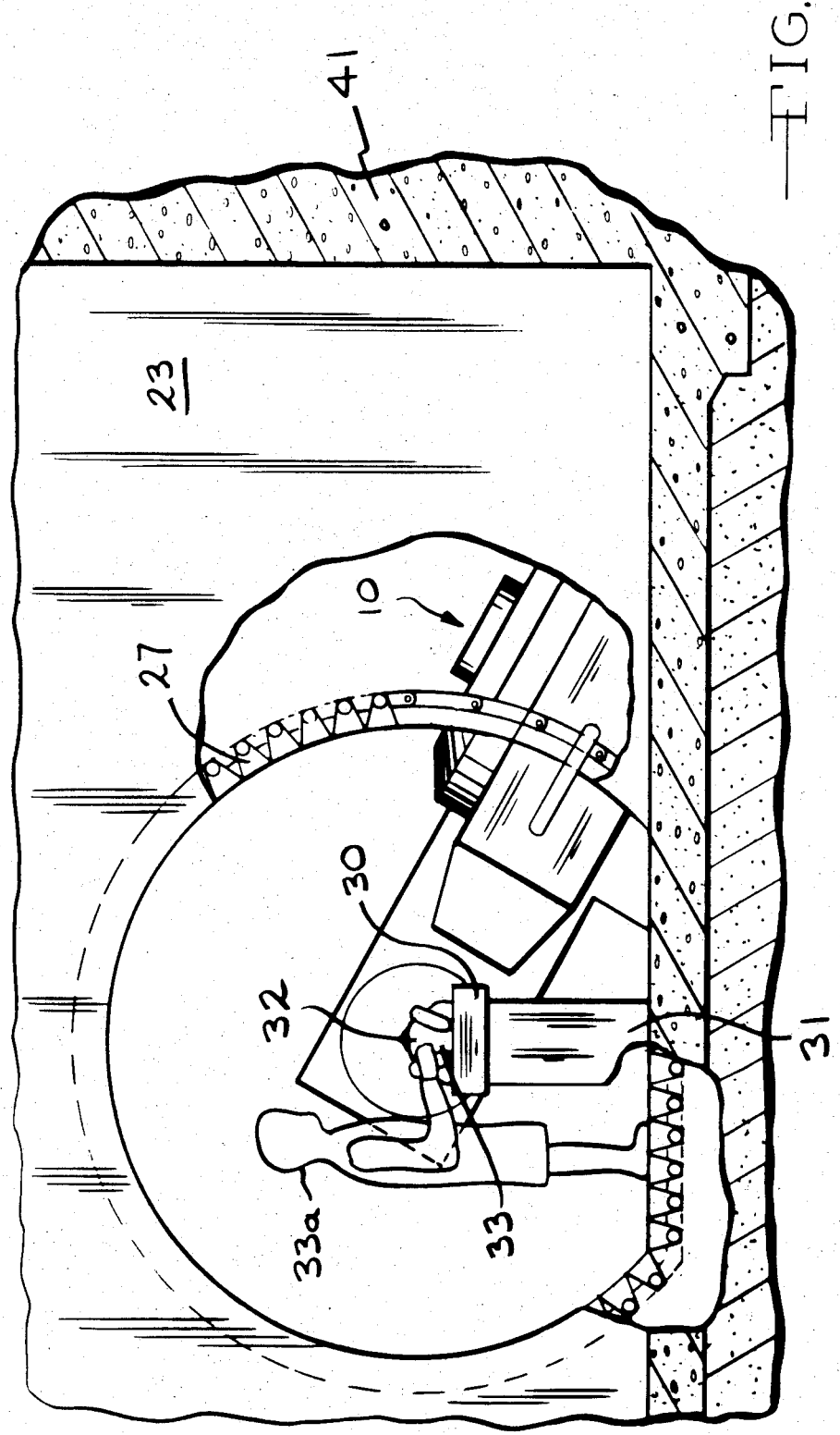

FIG. 9 is a left front view of the cyclotron (10) shown in FIG. 8 in partial section, particularly illustrating the positioning of a technician (33a) and a patient (33).

Figure 10:
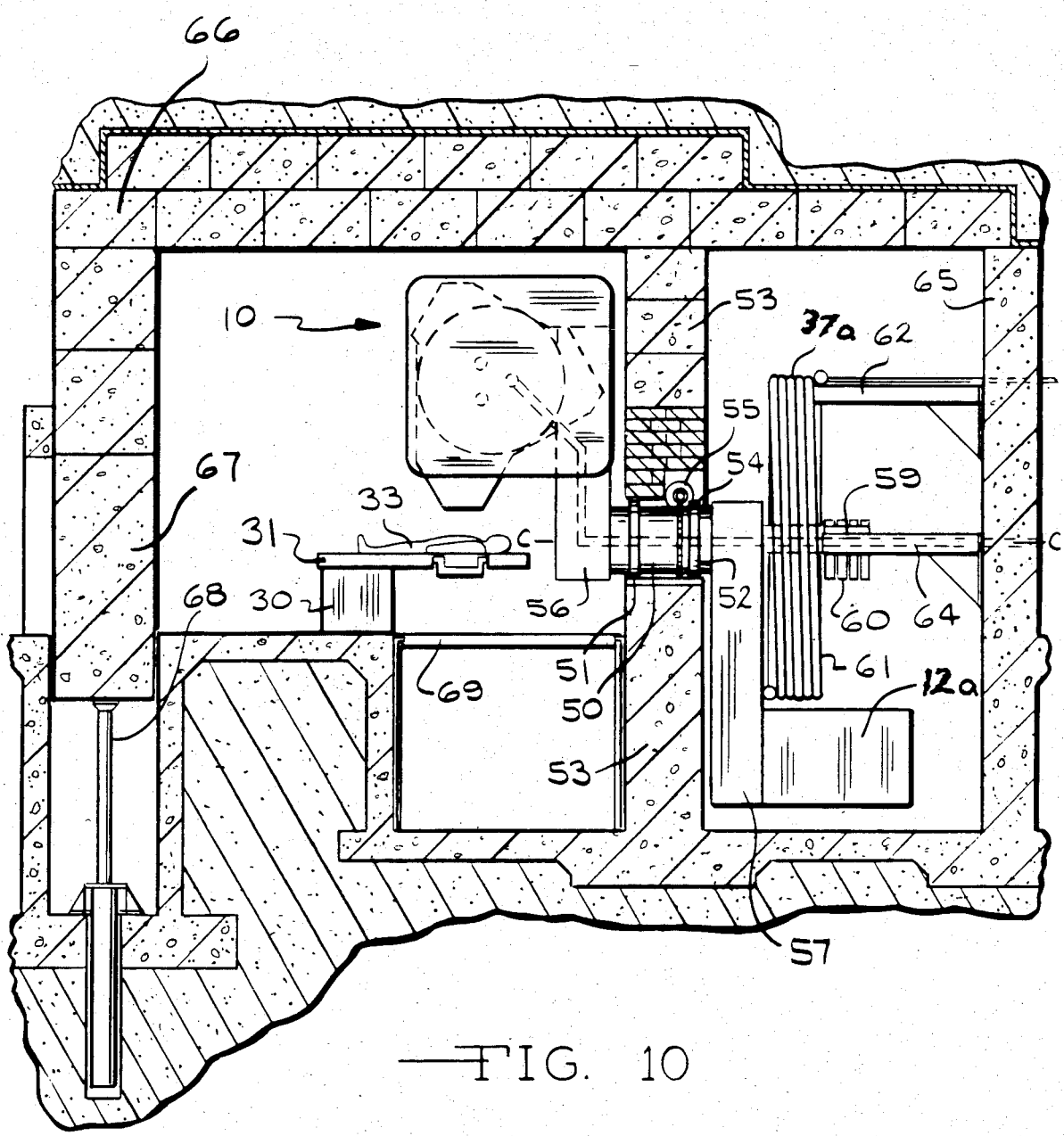
Figure 11:
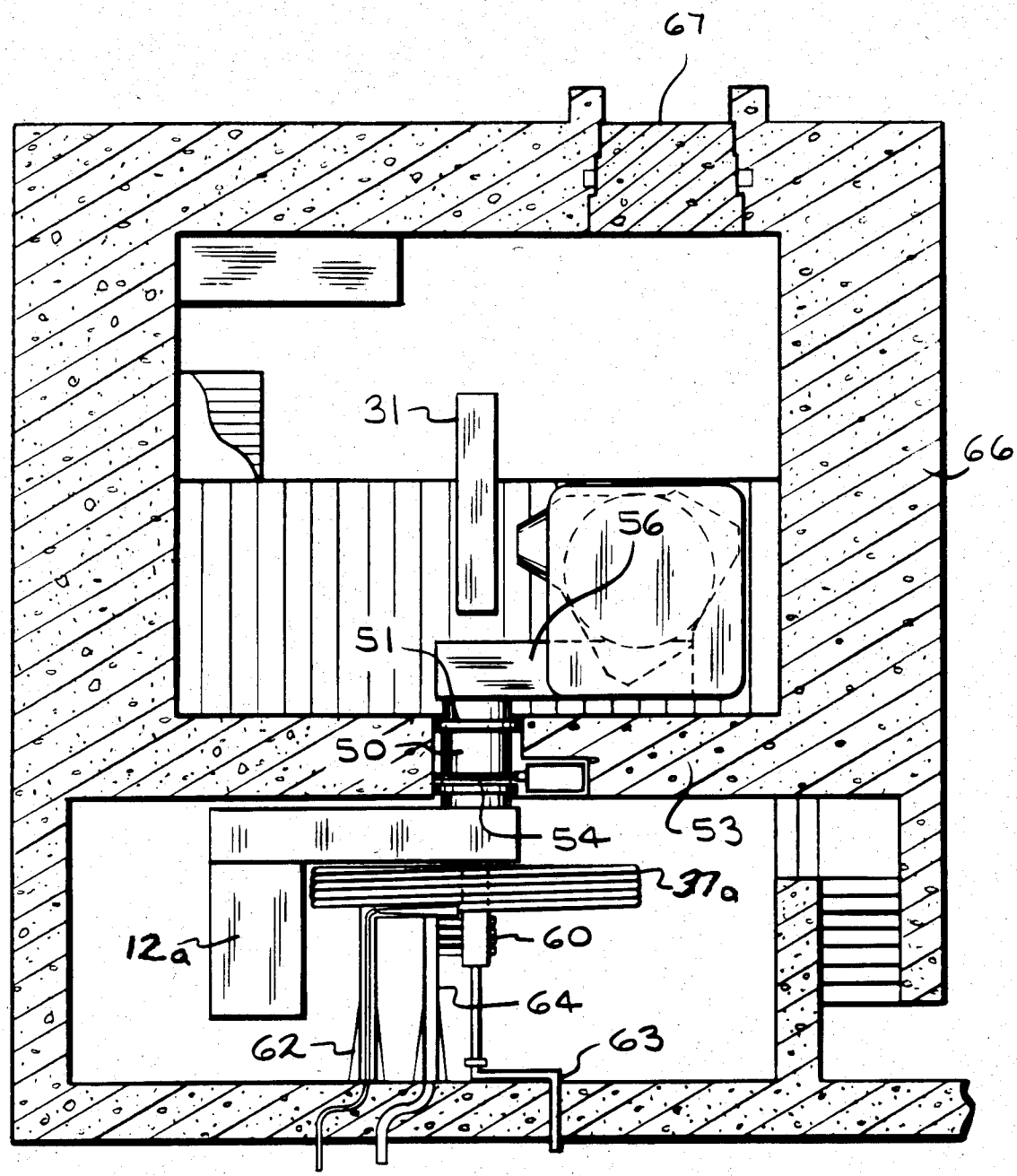

FIGS. 10 and 11 illustrate an alternative embodiment of the therapy cyclotron (10) utilizing a pair of segments (56, 57) mounted on opposite sides of a pivot means (50) with the cyclotron (10) and counterweight (12) at the ends of each of the segments.

Figure 12:
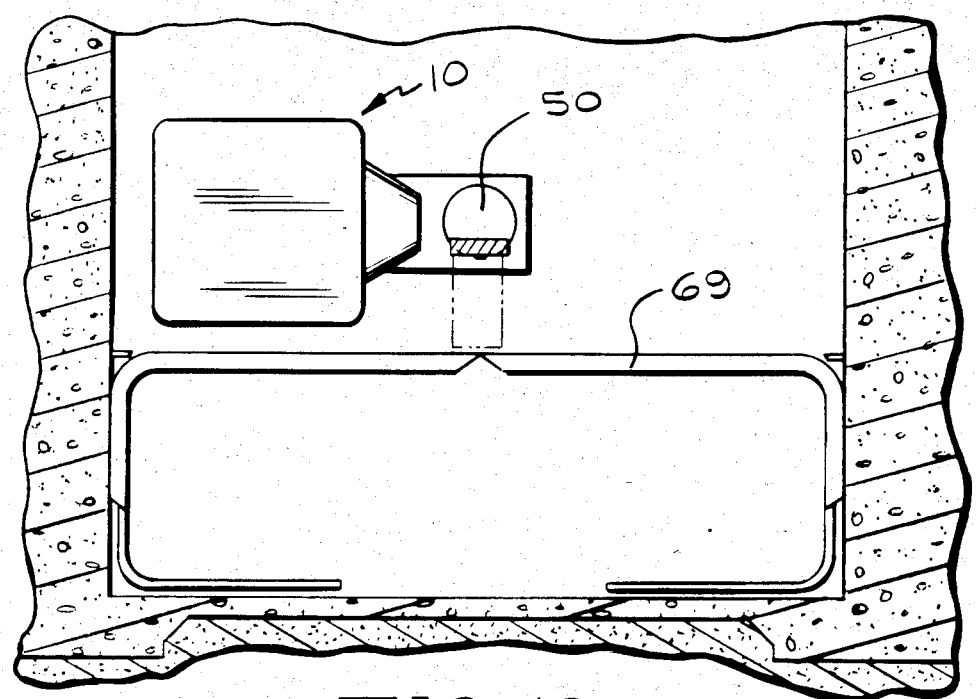
Figure 13:
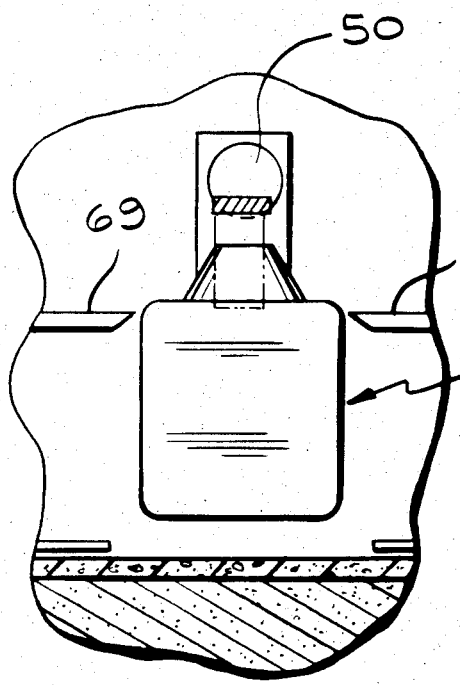
Figure 14:
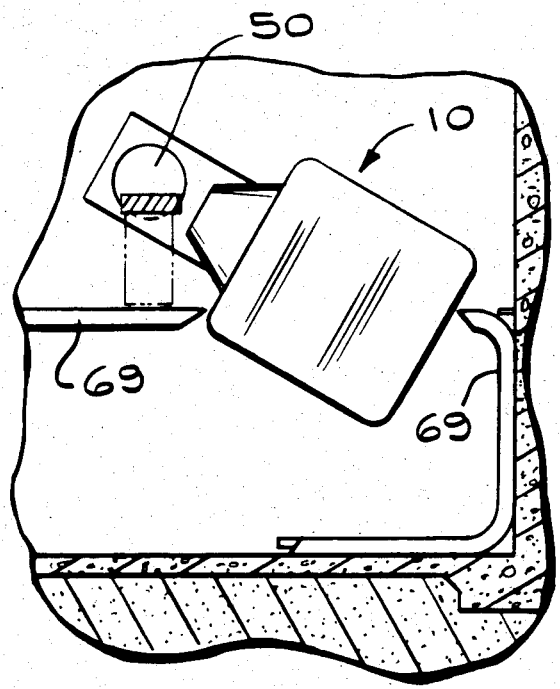

FIGS. 12, 13, and 14 are front cross-sectional views of FIG. 10, particularly showing the position of a standard prior art computer controlled movable floor (69) which moves as a function of the cyclotron (10) position during rotation.

GENERAL DESCRIPTION

The present invention relates to a superconducting cyclotron (10) apparatus which generates a beam (113) of high velocity atomic particles or subparticles to be directed at an object to be irradiated from spirally accelerated charged atom particles around a cyclotron axis (a—a) which form the beam or which impinge upon a target (112) to produce the beam and including inlet and outlet conduit means (121) for supplying and removing liquified gas to and from a vessel (105) around superconducting coils (101, 101a) supplied by electrical leads (119, 119a) inside the vessel which pass around spaced apart iron poles (100, 100a) so as to generate a magnetic field between the poles when current is supplied to the coils and which function to produce the spirally accelerated charged atomic particles with an oscillatory electrical field, the improvement which comprises:

a Joule-Thompson effect constricted capillary tube (200) leading to a semi-circular tube (123) adjacent to and in heat transfer relationship with both coils and the liquified gas in the vessel, with the semi-circular tube connected to an exit tube (201) from the vessel and cyclotron, wherein in operation of the cyclotron liquified gas is at an elevated pressure $P_1$ in the vessel and a portion of the liquified gas in the vessel flows through the capillary tube and expands into the semi-circular tube at a pressure $P_2$ lower than $P_1$ thus cooling the semicircular tube and thus the liquified gas in the vessel and the coils and then the liquified gas is removed through the exit tube, and wherein the cooled semi-circular tube subcools the liquified gas in the coil vessel thus preventing the formation of bubbles in this vessel due to heat flowing into the liquified gas in the vessel along the electrical leads (119, 119a) supplying current to the coils.

The present invention also relates to a superconducting cyclotron (10) apparatus which generates a beam (113) of high velocity atomic particles or subparticles directed at an object to be irradiated by spirally accelerated charged atomic particles around a cyclotron axis (a—a) which impinge upon a target (112) to produce the beam, with windows (114, 114a), and a collimator (116, 117) on a first side of the cyclotron tangental to the spirally accelerated charged atomic particles for defining the beam, including a support structure having a counterweight (12) for the cyclotron so as to be rotatable on a rotation axis (b—b) between the cyclotron and counterweight for changing the angle of the beam in an arc defining a plane around the rotation axis so that an object on the axis can be irradiated, and including inlet and outlet conduit means (121) for supplying and removing a liquified gas to and from a vessel (105) with superconducting coils (101, 101a) in the vessel which pass around spaced apart iron poles (100, 100a) so as to generate a magnetic field between the poles when current is supplied to the coils and with an iron yoke (102) connecting the poles outside the coils so as to return the magnetic field between the poles, wherein the poles and coils function to produce the spirally accelerated charged atomic particles with an oscillating electrical field produced by electrodes, the improvement in the yoke which comprises:

an iron or steel yoke (102) having sections which are essentially the same in external configuration over an angle of 120° around the cyclotron axis including (a) three first flat exterior faces (155) of the yoke which are parallel to the cyclotron axis and tangential to first radii from the cyclotron axis and symmetrical at equal arcs around the cyclotron axis and (b) three second flat exterior faces (156) of the yoke equal in number to the first faces which are parallel to the cyclotron axis and tangential to second radii from the cyclotron axis shorter than the first radii and are tangential in an opposite direction from the first faces so that the flat faces intersect at a third radii from the cyclotron axis to form three lobes (157), wherein the first and second flat surfaces provide for mounting of electrical, target and liquified gas connections to the inlet conduit means to the cyclotron and reduce the weight of the cyclotron over a cyclotron having a cylindrically faced yoke with a diameter of the third radii.

The present invention further relates to a superconducting cyclotron (10) apparatus which generates a beam of high velocity atomic particles or subparticles directed at an object to be irradiated by spirally accelerated charged atomic particles around a cyclotron axis (a—a) which impinge upon a target (112) to produce the beam, with windows (114 114a) and a collimator (116, 117) on a first side of the cyclotron tangental to the spirally accelerated charged atomic particles for defining the beam, including a support structure mounting a counterweight (12) for the cyclotron and rotatable on a rotation axis (b—b) between the cyclotron and counterweight for changing the angle of the beam in an arc defining a plane around the rotation axis so that an object on the axis can be irradiated and including inlet and outlet conduit means (121) for supplying and removing a liquified gas to and from a vessel (105) with superconducting coils (101, 101a) in the vessel which pass around spaced apart iron poles (100, 100a) which can generate a magnetic field between the poles when current is supplied to the poles and with an iron or steel yoke (102) between the poles for returning the magnetic field between the poles, wherein the poles and coils function to produce the spirally accelerated charged atomic particles with an oscillating electrical field produced by electrodes, the improvement which comprises:

a yoke (102) with faces (155, 156) parallel to the cyclotron axis and having sections which are essentially the same in external configuration over angles of 120° around the cyclotron axis.

Preferably the apparatus includes a yoke having sections which are essentially the same in external configuration over an angle of 120° around the cyclotron axis including (a) three first flat exterior faces (155) of the yoke which are parallel to the cyclotron axis and tangential to a first radius from the cyclotron axis and symmetrical at equal arcs around the cyclotron axis; and (b) three second flat exterior faces (156) of the yoke equal in number to the first faces which are parallel to the cyclotron axis and tangential to second radii from the cyclotron axis shorter than the first radii and are tangential in an opposite direction from the first faces so that the flat faces intersect at a third radii from the cyclotron axis to form three lobes (157), wherein the first and second flat faces provide for mounting of electrical, target and liquified gas connections to the inlet means to the cyclotron.

Also preferably retaining members (137) for the coils are mounted through the first faces of the yoke supporting both coils at angles of 120° around the cyclotron axis, wherein, the window and the collimator are provided through one first flat face of the yoke, wherein electrical leads to the coils are provided through another first flat face 120° from the first flat face, wherein the liquified gas inlet and outlet means (121) is provided through a final first flat face 240° and wherein the liquified gas outlet is provided through a second flat face so that the weight and magnetic field is approximately equally distributed around the cyclotron axis.

The present invention also relates to a superconducting cyclotron (10) apparatus which generates a beam (113) of high velocity atomic particles or subparticles to be directed at an object to be irradiated from spirally accelerated charged atomic particles which impinge upon a target (112) to produce the beam, with windows (114, 114a) and a collimator (116, 117) on a first side of the cyclotron tangential to the spirally accelerated charged particles for defining the beam including a support structure having a counterweight (12) for the cyclotron rotatable in two directions on a rotation axis (b—b) between the counterweight and cyclotron for changing the angle of the beam in an arc defining a plane around the rotation axis so that an object on the axis can be irradiated and further including inlet and outlet conduit means (121) for supplying and removing liquified gas to and from a vessel (105) and with superconducting coils (101, 101a) in the vessel which pass around spaced apart iron poles (100, 100a) which can generate a magnetic field between the poles when current is supplied to the coils and which functions to produce the spirally accelerated charged particles with an oscillating electrical field, the improvement which comprises:

(a) flexible hose (37) in the form of a helical coil defining a diameter about the pivot axis and attached at the inlet and outlet conduit means so that upon rotation of the cyclotron on the rotation axis the diameter of the coil increases in one direction and decreases in the opposite direction; and (b) spring means (38) attached to and supporting the helically coiled hose.

The present invention also relates to a superconducting cyclotron (10) apparatus which generates a beam of high velocity atomic particles or subparticles to be directed at an object to be irradiated from spirally accelerated charged atomic particles which impinge upon a target (112) to produce the beam, with a window (114) and a collimator (116, 117) on a first side of the cyclotron tangential to the spirally accelerated charged particles for defining the beam including a support structure having a counterweight (12) for the cyclotron rotatable in two directions on a rotation axis (b—b) between the counterweight and cyclotron for changing the angle of the beam in an arc defining a plane around the rotation axis so that an object on the axis can be irradiated and further including inlet and outlet conduit means (121) for supplying and removing liquified gas to and from a vessel (105) and with superconducting coils (101, 101a) in the vessel wound around spaced apart iron poles (100, 100a) which can generate a magnetic field between the poles when current is supplied to the coils and which functions to produce the spirally accelerated charged particles with an oscillating electrical field, the improvement which comprises:

(a) two elongate segments (56, 57) on either side of and along the rotation axis so as to be 180° apart with ends on each segment including a counterweight (12) at the end of one segment and a cyclotron (10) at the end of the other segment opposite the counterweight, such that the beam can be generated in a plane perpendicular to and in the direction of the rotation axis;

(b) pivot means (50) supporting the segments at the rotation axis with the cyclotron balancing the counterweight and with the rotation axis providing a fulcrum such that the segments are rotatable in an arc in the plane perpendicular to the pivot axis;

(c) drive means (55) for rotating the segments in the arc about the rotation axis and the pivot means as the beam is generated;

(d) flexible hose (37) in a helical coil about the rotation axis attached at the inlet and outlet conduit means of the cyclotron for supplying and removing a liquified gas to and from the vessel and coils; and (e) spring means (38) supporting the hose in the helical coil.

The present invention also relates to a superconducting cyclotron (10) apparatus which generates a beam (113) of high velocity atomic particles or subparticles to be directed at an object to be irradiated from spirally accelerated charged atomic particles which impinge upon a target (112) to produce the beam, with windows (114, 114a) and a collimator (116, 117) on a first side of the cyclotron tangential to the spirally accelerated charged particles for defining the beam including a support structure having a counterweight (12) for the cyclotron rotatable in two directions on a rotation axis (b—b) between the counterweight and cyclotron for changing the angle of the beam in an arc defining a plane around the rotation axis so that an object on the axis can be irradiated and further including inlet and outlet conduit means (121) for supplying and removing liquified gas to and from a closed vessel (105) and with superconducting coils (101, 101a) in the vessel which pass around spaced apart iron poles (100, 100a) which can generate a magnetic field between the poles when current is supplied to the coils and which functions to produce the spirally accelerated charged particles with an oscillating electrical field, the improvement which comprises:

(a) dual spaced apart parallel rings (11, 11a) each rigidly supporting the counterweight and cyclotron so as to be 180° from each other such that the cyclotron can be rotated by the rings about the rotation axis which is defined by the centers of the rings;

(b) rollers (13, 13a, 13c, 13d) mounting the rings for rotation of the rings about the rotation axis; and (c) drive means (14) for rotating the rings. Preferably the apparatus includes flexible hose (37) in a helical coil about the rotation axis attached to the inlet and outlet of the conduit means for supplying and removing the liquid gas to and from the closed vessel and coils and spring means (38) attached to and supporting the hose in the helical coil.

The present invention also relates to a superconducting cyclotron (10) apparatus which generates a beam (113) of high velocity atomic particles or subparticles to be directed at an object to be irradiated from spirally accelerated charged atomic particles which impinge upon a target (112) to produce the beam, with a window (114) and a collimator (116, 117) on a first side of the cyclotron tangential to the spirally accelerated charged particles for defining the beam including a support structure having a counterweight (12) for the cyclotron rotatable in two directions on a rotation axis (b—b) between the counterweight and cyclotron for changing the angle of the beam in an arc defining a plane around the rotation axis so that an object on the axis can be irradiated and further including inlet and outlet conduit means (121) for supplying and removing liquified gas to and from a vessel (105) and with superconducting coils (101, 101a) in the vessel which pass around spaced apart iron poles (100, 100a) which can generate a magnetic field between the poles when current is supplied to the coils and which functions to produce the spirally accelerated charged particles with an oscillating electrical field, the improvement which comprises:

an essentially cylindrically shaped rotatable floor of articulated slats (27) having a longitudinal axis of rotation which is mounted adjacent to the support structure around the cyclotron and counterweight so that the longitudinal axis of the floor and rotational axis of the support structure are the same and so that the floor rotates with the support structure.

Cyclotron

Referring to FIGS. 1 and 2, the cyclotron 10 has large iron poles 100 and 100a with pole tips or faces 100c and 100d with superconducting coils 101 and 101a around the poles 100 and 100a and with iron yoke 102 and pole caps 103 and 104 defining a magnetic field return loop. The coils 101 and 101a are cooled with a liquified gas at near 0° K., such as by liquid helium, in a helium vessel 105. This renders the coils 101 and 101a superconductive and thus reduces the weight of the cyclotron per MeV of the output beam. A vacuum wall 105a is provided around vessel 105.

Positive ion acceleration is achieved with three identical spaced apart electrodes or dees 106 each dee containing a gap 107 and all contained in a vacuum chamber 108. The dees 106 are connected to a high-frequency, high-voltage oscillator circuit through RF coupling loop 109 which joins one of the three pairs of dee stems 110 and 110a. The dee stems 110 and 110a are the inner conductor of a quarter wave transmission line, the electrical length of which is determined by the position of the clamped but adjustable short circuit connection 110b between dee stem 110a and the outer surface and iron cap 104 with copper lined wall 104a, this electrical length being adjusted so that the complete dee 106 and dee stems 110 and 110a define a system has a natural resonance at a frequency which provides acceleration of the atomic particles 113. The rapidly alternating RF field is provided between each of the three dees 106 and the outer wall 104a by the circuit and coupling loop 109.

Positive ions are provided by an ion source 111 at the center of the evacuated vacuum chamber 108. The magnetic field between poles 100 and 100a is perpendicular to the plane defined by the middle of the accelerating gap 107 in the three dees 106. The electrical field between the dees 106 and the tips 100c and 100d of adjacent poles 100 and 100a is phased such that an ion is accelerated by each dee 106 in succession as it leaves the ion source 111. The magnetic field between the tips 100c and 100d forces the ion into a spiral path. The magnetic field is proportioned and the electric field between the dees 106 and the adjacent pole tips 100 and 100a is phased such that the ion from the ion source 111 is accelerated by each dee 106 in succession, as it passes in the multiturn spiral orbit from ion source 111 to the target 112. The ion hits a target 112 tangentially to produce neutrons 113 which escape through a window 114 housed in a holder 115 through collimators 116 and 117 as a beam 113.

The liquified gas is supplied to the vessel 105 by coaxial inlet and outlet conduit 121. The vessel 105 is further cooled internally by semi-circular tube 123 as discussed hereinafter. The liquified gas system is essentially closed except for the semi-circular tube 123.

RF coupling loop 109 is connected through vacuum insulator 124 mounted in housing 125 mounted in the iron pole cap 103. The loop 109 is powered by a conventional RF system. Plugs 126 close the openings 127 and 128.

The target 112 is provided with a vacuum lock 129 for removal of the target 112 for replacement. Similarly the ion source 111 is provided with a vacuum lock 130 for replacement of parts of the ion source 111 the vacuum lock valve 133 using angle gears 131 and 132 connected to rods 134 and 135. These are conventional features of a cyclotron.

The coils 101 and 101a are wound on bobbins 136, which become part of the liquified helium vessel 105 after covers are attached and sealed. The helium vessel 105 is supported inside the vacuum wall 105a by means of folded support columns 137 held in place by iron plugs 138. The folded columns include an uneven number of tubes 139, 140 and 141 such that the center tube 140 is in tension and the inner and outer tubes 139 and 141 are in compression. The vessel 105a is provided with extensions 105b to accommodate the columns 137.

The helium vessel 105 is provided with a rupturable safety vent 142 and tube 120 for removal of the liquified gas in the event of boiling of the liquified gas. Non-magnetic plugs 143 and 144 provide 120° magnetic symmetry with the opening for the large collimator 116 as do the magnetic plugs 138 for the folded columns. The conduit 120 is 120° symmetrical with coil leads 119a and non-magnetic plug 152. Non-magnetic plug 145 balances the coaxial inlet and outlet helium conduit 121 and target 112 for 120° symmetry.

The beam 113 path includes a mirror 146 which reflects light in the beam path. Hinged light 147 is at the same distance from the mirror 146 as the target 112 so that light reflected from the mirror 146 follows the same path as the beam 113. Hinge 148 is mounted on the collimator support 149. The collimators 116 and 117 are removable in order to change the width of the beam 113. Dosimeters 150 are provided to measure the beam 113 flux. Magnetic plug 151 provides access to the dosimeter 150. Since the plug 151 is magnetic it does not disturb the 120° magnetic symmetry.

The cyclotron 10 is provided with a pop-up target 153 supported by hydraulic ram 154. The pop-up target 153 is used to monitor the spirally accelerated charged particles before they hit the target 112. A puller 154 is used to extract the atomic projectiles from the ion source 111. A fixed position basic superconducting cyclotron having a circular yoke is in operation at Michigan State University, East Lansing, Mich. The novel feature of the cyclotron of the present invention is in the configuration of the yoke 102 with 120° symmetry and the use of the semi-circular cooling tube 123 which subcools the main helium bath so that the vessel 105 can be inverted without developing gas pockets from boiling of the liquified gas.

The yoke 102 includes three first exterior flat faces 155 which are parallel to the cyclotron axis a—a and tangential to first radius $r_1$ from the axis a—a. The faces are symmetrical at 120° points around the 360° around the axis a—a. Three second flat exterior faces 156 which are also parallel to the cyclotron axis a—a are provided which are tangential to a second radius $r_2$ from the axis a—a in an opposite direction from the first faces 155 such that the faces 155 and 156 intersect to form three lobes 157. The faces 155 and 156 provide flat surfaces for mounting of electrical, target and gas connections to the cyclotron. The folded columns are easily mounted on the helium vessel 105 through the faces 155.

Figure 3:
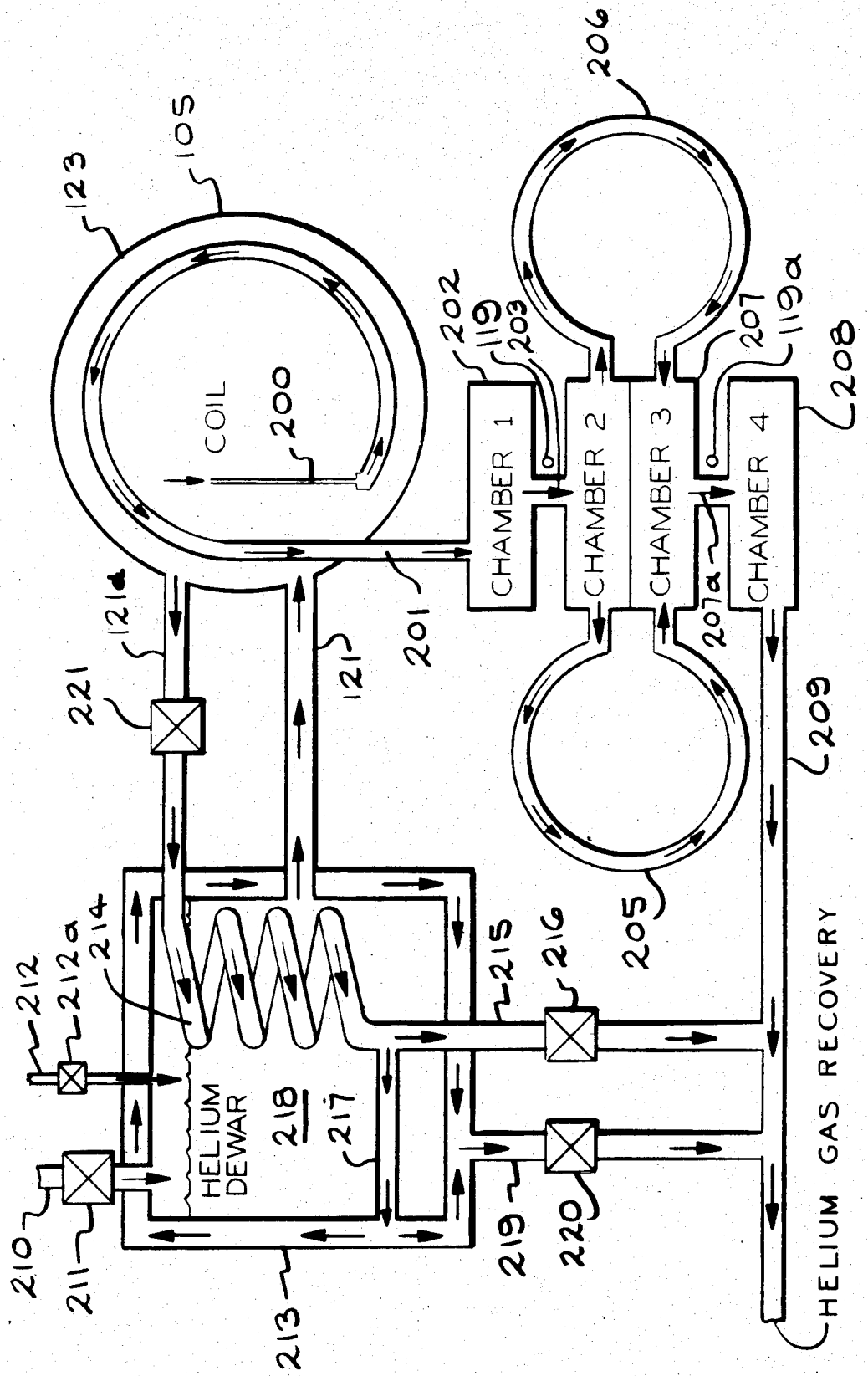
FIG. 3 is a schematic view of a supplementary cooling system for the coils (101, 101a) particularly illustrating a capillary tube (200) leading into a semicircular tube (123) and then leading into an exit tube (201) which allows expansion of the liquified gas in the semi-circular tube with resultant subcooling of the liquified gas in the vessel (105) and the coils.

FIG. 3 shows a schematic view of a system for subcooling the liquified gas in the vessel 105. The Joule-Thompson effect is utilized by providing a constricted capillary tube 200 which leads into semi-circular tube 123. The pressure drop in passing through the constricted capillary tube 123 takes the liquified gas from vessel 105 to a pressure corresponding to its normal boiling point at the temperature of the vessel 105 and the boiling of the liquified gas in tube 123 then provides subcooling through the wall of the tube 123 for the main body of liquified gas in the vessel 105. The tube 123 is connected to an exit tube 201 from the main helium vessel 105 and leads to a chamber 202 which channels the boil off gas into a heat exchange conduit 203 cooling a first section of the coil electrical leads 119 and then is provided to a second chamber 204 which leads to conduits 205 and 206 which cool a radiation shield (not shown) between vessel 105 and the vacuum wall 105a and then are returned to a third chamber 207 leading to a conduit 207a cooling a second section of the coil electrical leads 119a and then to a fourth chamber 208 which vents to a helium gas recovery system or to the atmosphere by line 209. Liquified gas is supplied from a helium dewar which is filled with purchased liquid helium by a fill line 210 and valve 211 or alternatively filled from a refrigerator. A separate line 212 with valve 212A is provided to raise the pressure of the liquified gas stored in the dewar 218 so that the liquid is forced to flow through the coaxial supply and return tube 121 and into the coil vessel 105. Some return gas returns from the coils 106 and 106a through the outer coaxial line 121A, the flow regulated by valve 221, which also serves as a Joule-Thompson valve, lowering the pressure of the liquified gas to a pressure corresponding to the normal boiling point of the liquid at the temperature of the dewar 218 bath. Boil-off gas from the two-phase boiling liquid in coil 214 is divided by valves 216 and 220 so that as much of the gas as is needed is used to cool radiation shield 213 on the helium dewar 218. Finally, all gas returns to the room temperature recovery line 209 through either line 215 or line 219.

When helium is used as the liquid gas, Table I shows the pressures and temperatures of the helium in the system.

TABLE I

|  | P(psig) | T °K. |
| --- | --- | --- |
| Dewar Vessel 218 | | |
| Top(Vapor Region) | 10 | 4.8-300 |
| Bottom (Liquid Region) | 10 | 4.2 |
| tube 123 | 2.8 | 4.4 |
| first chamber 202 | 2.5 | 4.4 |
| second chamber 204 | 1.5 | 60 |
| third chamber 207 | 1.2 | 70 |
| fourth chamber 208 | 0.2 | 300 |
| line 209 | 0.0 | 300 |
| Dewar Coil 214 | 1.0 | 4.3 |
| cyclotron inlet 121 | 10 | 4.4 |
| Joule-Thompson Effect | | |
| valve 221 | 10-1.5 | 4.4-4.3 |
| coil vessel 105 | 10 | 4.4 |
| pressurizer line 212 | 10 | 300 |

As can be seen the liquified gas enters the cyclotron in an inlet conduit 121 into vessel 105 to cool the coils 101 and 101a. A portion of the liquified gas expands through the constricted capillary tube 200 into semi-circular tube 123 thereby reducing the temperature of the liquified gas in the vessel 105 below its boiling point so that the liquified gas is subcooled thus preventing boiling and the formation of gas pockets in the region containing the coils 101 and 101a. The liquified gas is removed by exit line 201, cooling the inner section of the coil leads 119, the upper and lower coil heat shields (not shown), the outer section of the coil leads 119a and then is vented or recovered via line 209. The liquified gas is provided to inlet line 121 by means of a Dewar vessel 218 which is conventional. The dewar 218 is filled from commercial sources through filling line and valve 210. A conventional refrigeration system can also be used. It is to be noted that only a small amount of helium gas is supplied via line 212 by opening valve 212a in order to maintain the system under pressure and this helium gas does not materially raise the temperature of the liquified gas in the main part of vessel 218.

As can be seen the use of the semi-circular tube 123 is uniquely suited for use with a movable cyclotron 10 and prevents boiling of the liquified gas around the coils 101 and 101a. This system thus enables the rotation of the cyclotron around 360° for therapeutic use as described hereinafter.

SUPPORT STRUCTURES

FIGS. 4 to 9 show the preferred support structure of the superconducting cyclotron 10. The cyclotron 10 is mounted between parallel spaced apart rings 11, 11a with a counterweight 12 at a position 180° around the rings 11. The rings 11 and 11a are mounted on four rollers 13, 13a, 13c and 13d, two for each ring 11. A ridge 11b of rings 11 and 11a rides in a recess 13b of rollers 13, 13a, 13c and 13d. One roller 13a is provided with a drive motor 14 connected to a worm 15 and driven worm gear 16 (FIG. 8). In this manner the rings 11 and 11a can be rotated around 360°. The rollers 13, 13a, 13c and 13d are mounted on supports 17 by shafts 18 for rotation. The supports 17 are mounted on I beam 19 located on a concrete floor 20. A recess 21 in floor 20 provides for rotation of the cyclotron 10 and counterweight 12.

Walls 22 and 23 are provided along either side of and facing rings 11 and 11a. A circular roller track 24 (FIGS. 4a and 5a) is mounted on the walls 22 and 23 which support rubber faced rollers 25 on shafts 26 connected to multiple connected slats 27 positioned around the rings 11 and 11a. The slats 27 thus form a cylindrical ring with a flattened side 28 (FIG. 8) providing the floor. A drive linkage 29 between the floor and the rings 11 and 11a provides movement of the floor upon movement of the cyclotron 10.

A patient table 30 and support 31 is provided along the rotation axis b—b so that the beam 113 from the cyclotron 10 impinges on a selected point 32 in a patient 33. The flattened section 28 of the floor 27 supports a technician 33a.

Helium, water, air, electricity, and other needed utility supplies are supplied to the cyclotron 10 through an arm 34 adjacent the cyclotron 10. The first arm 34 is connected to a central shaft 35 along the axis of rotation (b—b) and then to a second arm 36 which is 180° around the central shaft 35 which in turn connects a flexible hose 37 in the form of a helical coil. The hose 37 is supported by a spring 38 with holding clips 38a also in a helical coil. The spring 38 rides on rollers 39 supported by cantilevered arms 40 mounted on shielding wall 41. Thus as the cyclotron 10 rotates the diameter of the helical coil perpendicular to the axis b—b increases and decreases as shown in FIG. 6. FIG. 6 shows the hose 37 in solid lines with the cyclotron 10 at the 180° position (0° is at 12 o'clock) going counter-clockwise (positive) and in the 180° position clockwise (negative) in dashed lines. FIG. 7 shows the cyclotron 10 in a ninety degree position between the 0° and 180° positions of the rotation of the cyclotron 10. As also seen from FIGS. 6 and 7, the electrical, water, air, etc. leads 42 mounted on the second arm 36 wind around the shaft 35 to provide support for these leads 42. Couplers 43 and 45 are provided for the hose 37. The coupler 45 is fixed to the wall 41.

FIGS. 10 to 14 show a variation of the support structure for the cyclotron 10 wherein a pivot 50 on bearings 51 and 52 is supported by a wall 53. The pivot 50 includes a ring gear 54 driven by motor 55. On either side of the pivot 50 are provided first and second segments 56 and 57. A first segment 56 mounts the cyclotron 10 and a second segment 57 which is 180° around the rotational axis (c—c) mounts a counterweight 12a. An extension 59 of the pivot 50 along the axis (c—c) is provided to support electrical cables 60 which wrap around the extension 59. Flexible hose 37a for the liquified gas is provided in a helical coil and is supported by cantilever arms 62. The RF leads 63 lead into the extension 59 and through the pivot 50 and out the segment 56 to the cyclotron 10. The helium is supplied to the helically coiled hose 37a. A support 64 mounted on the wall 65 is provided from the electrical cables 60. The hose 37a connects to segment 57 and provides the liquified gas through the segment 57, pivot means 50 and segment 56 to the cyclotron 10. Basically the operation of the helically coiled hose 37a is as previously described. The cyclotron 10 is housed in a shielding chamber 66 with a door 67 which rises and lowers vertically by means of hydraulic unit 68. A conventional movable floor 69 opens as shown in FIGS. 13 and 14 to allow movement of the cyclotron 10 when positions are used where the cyclotron 10 would otherwise conflict with the floor.

System Specifications

Typical specifications for the medical cyclotron 10 system are given in Table II. All specifications correspond to component operating conditions which are well within the levels which have already been achieved in other fixed position superconducting cyclotrons using standard engineering techniques.

TABLE II
SYSTEM SPECIFICATIONS

| CYCLOTRON | |
|---|---|
| Magnetic Field: | center 4.6 tesla, hill 5.4 tesla |
| rf System: | frequency 105 Mhz, dee voltage ± 40 kV peak, rf power 25 kw |
| Vacuum: | source gas off $5 \times 10^{-6}$ torr, source gas on $1.5 \times 10^{-5}$ torr. |
| Beam Energy: | 50 ± 0.3 MeV deuterons |
| Maximum Beam Current: | Pop-in target 50 microamperes, Be target 20 microamperes |
| Beam Current Reproducibility: | for beam current greater than 5 microamps the beam current setting can reproduce to within 5% of the previous value when the cyclotron is turned on after an off period of up to 30 minutes (without adjustment of ion source parameters). |
| SUPPORT SYSTEM | |
| Rotation Range: | +180° to −175° (355° total travel) |
| Mechanical Rigidity: | The extended central axis of the neutron collimator will intersect with a single sphere of 3 mm dia irrespective of the gantry rotation angle |
| Rotation Speeds: | fast 90°/min.; slow 22 ½°/min |
| Angular Accuracy: | The readout of the gantry angle accurate to 0.5°. |
| NEUTRON FLUX | |
| Spatial Reproducibility: | The dose distribution at the isocenter can reproduce on five successive days within a total variation of 6%, as observed in a test performed with neutron collimator set for a 10 × 10 cm field at the isocenter and using a 17 member array of detectors, (one detector at the isocenter and four lines of four detectors extending from the central detector on lines perpendicular to the collimator axis at 1 cm spacing). |
| Angular Stability: | The neutron flux as measured at the isocenter can be constant to within 5% as the cyclotron is successively moved in 30° steps through its full angular range. |

OPERATION

At the beginning of a working day, cyclotron 10 start-up is as follows:

1. A magnet "START" button providing current to the coils (101, 101a) is pressed and approximately 10 minutes is allowed for the coils (101, 101a) to come to full current, the actual value of the current is continuously monitored using an ammeter (not shown).

2. With the magnet coils 101, 101a at operating current and the ion source 111 voltage and current controls set at operating values, a source "START" button is pressed. This will cause readings of approximately 1500 volts and 0 amps to show on source voltage and current meters (not shown). The amount of source gas to be ionized supplied to the source is then slowly increased by turning up a source gas control until an arc strikes, the striking point being identified by a sudden drop in voltage to a value of about 400 volts and a sudden rise in arc current to a level of approximately 2 amperes. After striking the source, the gas is next slowly reduced until the voltage reaches the operating value of about 700 volts at which point the current falls to a value of approximately 1.5 amps.

3. With the rf voltage control at a low level a plate power supply "START" button is pressed and a plate voltage indication of 15 kilovolts will appear on a plate voltage meter (not shown). An rf "START" button is then pressed and a low voltage will appear on a dee 106 voltage meter (not shown) corresponding to the setting of the rf drive voltage 109 control. With the pop-up target 153 "UP", the voltage is then raised to the operating value and beam currents will appear on a pop-up target 153 current meter (not shown).

4. If the beam 113 current is not at the level desired, the gas is adjusted, raising or lowering the deuterium fraction to raise or lower the current level.

5. A reproducibility check is made by turning off the rf drive voltage 109, waiting for some period and then turning back on, leaving all other controls at their previous settings. Beam current on the pop-up target 153 should go back to the previous value.

6. Next the pop-up target 13 is moved to the down position and the beam 113 should immediately appear on the main target 112 as shown by a current meter (not shown) and at the same time readings should appear on displays from the dose monitor detectors 150. These readings are checked for proper level, the rf drive voltage 109 is turned off and the cyclotron 10 is then ready for use. Subsequent patient exposures are then initiated by supplying the rf 109.

In the preferred operation of the cyclotron 10, positively charged deuteron particles or other positively charged atomic particles are accelerated in a helical path between dees 106 so as to hit the target 112 tangentially to release neutrons which pass through exit windows 114, 114a and through the collimators 116, 117 as a beam 113 which is directed at the target or patient 33. The deuterons or other particles hitting the target 112 are at between about 25 to 75 MeV, and for medical purposes preferably about 50 MeV.

We claim:

1. In a superconducting cyclotron apparatus which generates a beam of high velocity particles comprising atomic particles and subparticles thereof to be directed at an object to be irradiated from spirally accelerated charged particles around a cyclotron axis which form the beam or which impinge upon a target to produce the beam and including inlet and outlet conduit means for supplying and removing liquified gas to and from a vessel around superconducting coils supplied by electrical leads inside the vessel which pass around spaced apart iron poles so as to generate a magnetic field between the poles when current is supplied to the coils and which function to produce the spirally accelerated charged particles with an oscillatory electrical field, the improvement which comprises:

a Joule-Thompson effect constricted capillary tube leading to a semi-circular tube adjacent to and in heat transfer relationship with both coils and the liquified gas in the vessel, with the semi-circular tube connected to an exit tube from the vessel and cyclotron, wherein in operation of the cyclotron liquified gas is at an elevated pressure $P_1$ in the vessel and a portion of the liquified gas in the vessel flows through the capillary tube and expands into the semi-circular tube at a pressure $P_2$ lower than $P_1$ thus cooling the semicircular tube and thus the liquified gas in the vessel and the coils and then the liquified gas is removed through the exit tube, and wherein the cooled semi-circular tube subcools the liquified gas in the coil vessel thus preventing the formation of bubbles in this vessel due to heat flowing into the liquified gas in the vessel along the electrical leads supplying current to the coils.

2. The superconducting cyclotron of claim 1 wherein the cyclotron is mounted on a rotatable support structure with a counterweight for the cyclotron on the support structure opposite the cyclotron, wherein the support structure is rotatable on a rotation axis between the cyclotron and counterweight for changing the angle of the beam in an arc defining a plane about the axis so that an object positioned at the axis can be irradiated.

3. The superconducting cyclotron of claim 2 wherein the rotatable support structure is a balance bar having two segments joined to a pivot means along the rotation axis and defining the rotation axis intermediate to opposite ends of the bar and wherein the cyclotron and counterweight are positioned on opposite ends of the balance bar.

4. The superconducting cyclotron of claim 3 wherein the segments of the balance bar are mounted on either side of the pivot means along the rotation axis.

5. The superconducting cyclotron apparatus of claim 2 wherein the rotatable support structure includes the cyclotron and counterweight both mounted on two spaced apart rings each having a center on the rotation axis and wherein each of the rings is mounted on rollers which provide rotation of the rings, cyclotron and counterweights around the rotation axis.

6. In a superconducting cyclotron apparatus which generates a beam of high velocity particles comprising atomic particles and subparticles thereof directed at an object to be irradiated by spirally accelerated charged particles around a cyclotron axis which impinge upon a target to produce the beam, with a window and a collimator on a first side of the cyclotron tangental to the spirally accelerated charged particles for defining the beam, including a support structure having a counterweight for the cyclotron so as to be rotatable on a rotation axis between the cyclotron and counterweight for changing the angle of the beam in an arc defining a plane around the rotation axis so that an object on the axis can be irradiated, and including inlet and outlet conduit means for supplying and removing a liquified gas to and from a vessel with superconducting coils in the vessel which pass around spaced apart iron poles so as to generate a magnetic field between the poles when current is supplied to the coils and with an iron yoke connecting the poles outside the coils so as to return the magnetic field between the poles, wherein the poles and coils function to produce the spirally accelerated charged particles with an oscillating electrical field produced by electrodes, the improvement in the yoke which comprises:

an iron or steel yoke having sections which are essentially the same in external configuration over an angle of 120° around the cyclotron axis including (a) three first flat exterior faces of the yoke which are parallel to the cyclotron axis and tangential to first radii from the cyclotron axis and symmetrical at equal arcs around the cyclotron axis and (b) three second flat exterior faces of the yoke equal in number to the first faces which are parallel to the cylotron axis and tangential to second radii from the cyclotron axis shorter than the first radii and are tangential in an opposite direction from the first faces so that the flat faces intersect at a third radii from the cyclotron axis to form three lobes, wherein the first and second flat surfaces provide for mounting of electrical, target and liquified gas connections to the inlet conduit means to the cyclotron and reduce the weight of the cyclotron over a cyclotron having a cylindrically faced yoke with a diameter of the third radii.

7. The superconducting cyclotron apparatus of claim 6 wherein the window and collimator are mounted through one of the first flat faces of the yoke.

8. The superconducting cyclotron apparatus of claim 6 wherein coil retaining members are mounted through the yoke at equal arcs around the cyclotron axis and engage bobbins mounting the coils and forming part of the vessel through each of the first or second flat faces of the yoke.

9. The superconducting cyclotron apparatus of claim 6 wherein coil retaining members are provided through each first flat faces, wherein the window and collimator are provided through one first flat face, wherein electrical leads to the coils are provided through another first flat face 120° from the initial first flat face and wherein a liquified gas inlet and outlet is provided through a final first flat face 240° from the initial first flat face and wherein liquified gas safety vent is provided through a first or second flat face so that the weight and magnetic field around the cyclotron axis is equally distributed.

10. In a superconducting cyclotron apparatus which generates a beam of high velocity particles comprising atomic particles and subparticles thereof directed at an object to be irradiated by spirally accelerated charge particles around a cyclotron axis which impinge upon a target to produce the beam, with a window and a collimator on a first side of the cyclotron tangental to the spirally accelerated charged particles for defining the beam, including a support structure mounting a counterweight for the cyclotron and rotatable on a rotation axis between the cyclotron and counterweight for changing the angle of the beam in an arc defining a plane around the rotation axis so that an object on the axis can be irradiated and including inlet and outlet conduit means for supplying and removing a liquified gas to and from a vessel with superconducting coils in the vessel which pass around spaced apart iron poles which can generate a magnetic field between the poles when current is supplied to the poles and with an iron or steel yoke between the poles for returning the magnetic field between the poles, wherein the poles and coils function to produce the spirally accelerated charged particles with an oscillating electrical field produced by electrodes, the improvement which comprises:

a yoke having sections which are essentially the same in external configuration over an angle of 120° around the cyclotron axis including (a) three first flat exterior faces of the yoke which are parallel to the cyclotron axis and tangential to a first radius from the cyclotron axis and symmetrical at equal arcs around the cyclotron axis;

(b) three second flat exterior faces of the yoke equal in number to the first faces which are parallel to the cyclotron axis and tangential to second radii from the cyclotron axis shorter than the first radii and are tangential in an opposite direction from the first face so that the flat faces intersect at a third radii from the cyclotron axis to form three lobes, wherein the first and second flat faces provide for mounting of electrical, target and liquified gas connections to the inlet means to the cyclotron;

(c) retaining members for the coils mounted through the first faces of the yoke supporting both coils at angles of 120° around the cyclotron axis, wherein, the window and the collimator are provided through one first flat face of the yoke, wherein electrical leads to the coils are provided through another first flat face 120° from the first flat face, wherein the liquified gas inlet and outlet means is provided through a final first flat face 240°.

11. The superconducting apparatus of claim 10 wherein the retaining members are circular cross-sectional folded support columns which engage bobbins supporting the coils as part of the vessel and wherein magnetic or non-magnetic structural support cores support the columns through the yoke.

12. In a superconducting cyclotron apparatus which generates a beam of high velocity particles comprising atomic particles and subparticles thereof to be directed at an object to be irradiated from spirally accelerated charged particles which impinge upon a target to produce the beam, with a window and a collimator on a first side of the cyclotron tangential to the spirally accelerated charged particles for defining the beam including a support structure having a counterweight for the cyclotron rotatable in two directions on a rotation axis between the counterweight and cyclotron for changing the angle of the beam in an arc defining a plane around the rotation axis so that an object on the axis can be irradiated and further including inlet and outlet conduit means for supplying and removing liquified gas to and from a vessel and with superconducting coils in the vessel which pass around spaced apart iron poles which can generate a magnetic field between the poles when current is supplied to the coils and which functions to produce the spirally accelerated charged particles with an oscillating electrical field, the improvement which comprises:

(a) flexible hose in the form of a helical coil defining a diameter about the pivot axis and attached at the inlet and outlet conduit means so that upon rotation of the cyclotron on the rotation axis the diameter of the coil increases in one direction and decreases in the opposite direction; and (b) spring means attached to and supporting the helically coil hose.

13. The apparatus of claim 12 wherein the counterweight and cyclotron are mounted on a balance bar with a pivot means mounted on the bar between the counterweight and cyclotron.

14. The superconducting cyclotron apparatus of claim 12 wherein the counterweight and cyclotron are mounted 180° apart between two spaced apart parallel rings and wherein the rings are mounted on rollers for rotation about the rotation axis.

15. The superconducting cyclotron apparatus of claim 12 wherein an essentially cylindrically shaped rotatable floor having a longitudinal axis of rotation is mounted adjacent to the support structure around the cyclotron and counterweight so that the longitudinal axis of the floor and rotation axis of the support structure are the same and so that the floor rotates with the support structure.

16. The superconducting cyclotron apparatus of claim 15 wherein the floor is composed of elongate sections joined together to articulate in the direction of rotation and wherein a horizontal flat floor surface is provided below the rotation axis of the support structure so that the elongate sections ride over the flat surface and flatten as the cyclotron is rotated.

17. In a superconducting cycltron apparatus which generates a beam of high velocity particles comprising atomic particles and subparticles thereof to be directed at an object to be irradiated from spirally accelerated charge particles which impinge upon a target to produce the beam, with a window and a collimator on a first side of the cyclotron tangential to the spirally accelerated charged particles for defining the beam including a support structure having a counterweight for the cyclotron rotatable in two directions on a rotation axis between the counterweight and cyclotron for changing the angle of the beam in an arc defining a plane around the rotation axis so that an object on the axis can be irradiated and further including inlet and outlet conduit means for supplying and removing liquified gas to and from a vessel and with superconducting coils in the vessel which pass around spaced apart iron poles which can generate a magnetic field between the poles when current is supplied to the coils and which functions to produce the spirally accelerated charged particles with an oscillating electrical field, the improvement which comprises:
    (a) two elongate segments on either side of and along the rotation axis so as to be 180° apart with ends on each segment including a counterweight at the end of one segment and a cyclotron at the end of the other segment opposite the counterweight, such that at the end of one segment and a cyclotron at the end of the other segment opposite the counterweight, such that the beam can be generated in a plane perpendicular to and in the direction of the rotation axis;
    (b) pivot means supporting the segments at the rotation axis with the cyclotron balancing the counterweight and with the rotation axis providing a fulcrum such that the segments are rotatable in an arc in the plane perpendicular to the pivot axis;
    (c) drive means for rotating the segments in the arc about the rotation axis and the pivot means as the beam is generated;
    (d) flexible hose in a helical coil about the rotation axis attached at the inlet and outlet conduit means of the cyclotron for supplying and removing a liquified gas to and from the vessel and coils; and
    (e) spring means supporting the hose in the helical coil.

18. In a superconducting cyclotron apparatus which generates a beam of high velocity particles comprising atomic particles and subparticles thereof to be directed at an object to be irradiated from spirally accelerated charged particles which impinge upon a target to produce the beam, with a window and a collimator on a first side of the cyclotron tangential to the spirally accelerated charged particles for defining the beam including a support structure having a counterweight for the cyclotron rotatable in two directions on a rotation axis between the counterweight and cyclotron for changing the angle of the beam in an arc defining a plane around the rotation axis so that an object on the axis can be irradiated and further including inlet and outlet conduit means for supplying and removing liquified gas to and from a closed vessel and with superconducting coils in the vessel which pass around spaced apart iron poles which can generate a magnetic field between the poles when current is supplied to the coils and which functions to produce the spirally accelerated charged particles with an oscillating electrical field, the improvment which comprises:
    (a) dual space apart parallel rings each rigidly supporting the counterweight and cyclotron so as to be 180° from each other such that the cyclotron can be rotated by the rings about the rotation axis which is defined by the centers of the rings;
    (b) rollers mounting the rings for rotation of the rings about the rotation axis;
    (c) drive means for rotating the rings;
    (d) flexible hose in a helical coil about the rotation axis attached to the inlet and outlet of the conduit means for supplying and removing the liquid gas to and from the closed vessel and coils; and
    (e) spring means attached to and supporting the hose in the helical coil.

19. In a superconducting cyclotron apparatus which generates a beam of high velocity particles comprising atomic particles and subparticles thereof to be directed at an object to be irradiated from spirally accelerated charged particles which impinge upon a target to produce the beam, with a window and a collimator on a first side of the cyclotron tangential to the spirally accelerated charged particles for defining the beam including a support structure having a counterweight for the cyclotron rotatable in two directions on a rotation axis between the counterweight and cyclotron for changing the angle of the beam in an arc defining a plane around the rotation axis so that an object on the axis can be irradiated and further including inlet and outlet conduit means for supplying and removing liquified gas to and from a closed vessel and with superconducting coils in the vessel which pass around spaced apart iron poles which can generate a magnetic field between the poles when current is supplied to the coils and which functions to produce the spirally accelerated charged particles with an oscillating electrical field, the improvement which comprises:
    (a) dual spaced apart parallel rings each rigidly supporting the counterweight and cyclotron so as to be 180° from each other such that the cyclotron can be rotated by the rings about a rotation axis defined by the centers of the rings;
    (b) rollers mounting the rings for rotation of the rings about the rotation axis; and
    (c) drive means for rotating the rings.

20. In a superconducting cyclotron apparatus which generates a beam of high velocity particles comprising atomic particles and subparticles thereof directed at an object to be irradiated by spirally accelerated charged particles around a cyclotron axis which impinge upon a target to produce the beam, with a window and a collimator on a first side of the cyclotron tangental to the spirally accelerated charged particles for defining the beam, including a support structure having a counterweight for the cyclotron so as to be rotatable on a rotation axis between the cyclotron and counterweight for changing the angle of the beam in an arc defining a plane around the rotation axis so that an object on the axis can be irradiated, and including inlet and outlet conduit means for supplying and removing a liquified gas to and from a vessel with superconducting coils in the vessel which pass around spaced apart iron poles so as to generate a magnetic field between the poles when current is supplied to the coils and with an iron or steel yoke connecting the pole outside the coils so as to return the magnetic field between the poles, wherein the poles and coils function to produce the spirally accelerated charged particles with an oscillating electrical field produced by electrodes, the improvement in the yoke which comprises:

a yoke with a number of flat surfaces, wherein the flat face are parallel to the cyclotron axis and having section which are essentially the same in external configuration over angles of 120° around the cyclotron axis.

21. In a superconducting cyclotron apparatus which generates a beam of high velocity particles comprising atomic particles and subparticles thereof to be directed at an object to be irradiated from spirally accelerated charged particles which impinge upon a target to produce the beam, with a window and a collimator on a first side of the cyclotron tangential to the spirally accelerated charged particles for defining the beam including a support structure having a counterweight for the cyclotron rotatable in two directions on a rotation axis between the counterweight and cyclotron for changing the angle of the beam in an arc defining a plane around the rotation axis so that an object on the axis can be irradiated and further including inlet and outlet conduit means for supplying and removing liquified gas to and from a vessel and with superconducting coils in the vessel which pass around spaced apart iron poles which can generate a magnetic field between the poles when current is supplied to the coils and which functions to produce the spirally accelerated charged particles with an oscillating electrical field, the improvement which comprises:

an essentially cylindrically shaped rotatable floor of articulated slats having a longitudinal axis of rotation which is mounted adjacent to the support structure around the cyclotron and counterweight so that the longitudinal axis of the floor and rotational axis of the support structure are the same and so that the floor rotates with the support structure.

* * * * *

UNITED STATES PATENT AND TRADEMARK OFFICE
CERTIFICATE OF CORRECTION

PATENT NO. : 4,641,104

DATED : February 3, 1987

INVENTOR(S) : Henry G. Blosser, Richard J. Burleigh, Gabe F. Blosser and Emanuel B. Jemison It is certified that error appears in the above-identified patent and that said Letters Patent are hereby corrected as shown below:

Column 3, line 7, the numeral "1" should be deleted.

Column 4, line 2, "tangental" should be --tangential--.

Column 4, line 49, "tangental" should be --tangential--.

Column 14, line 49, "tangental" should be --tangential--.

Column 15, line 44 "charge" should be --charged--.

Column 15, line 48 "tangental" should be --tangential--.

Column 16, line 9 "face" should be --faces--.

Column 16, line 59 "coil" should be --coiled--.

Column 17, line 13 "rotation" should be --rotational--.

Column 17, line 19 "charge" should be --charged--.

Column 18, line 16 "space" should be --spaced--.

Column 18, line 66 "tangental" should be --tangential--.

Column 19, line 11 "pole" should be --poles--.

Column 19, line 18 "face" should be --faces--.

UNITED STATES PATENT AND TRADEMARK OFFICE
CERTIFICATE OF CORRECTION

Page 2 of 2

PATENT NO. : 4,641,104

DATED : February 3, 1987

INVENTOR(S) : Henry G. Blosser, Richard J. Burleigh, Gabe F. Blosser and Emanuel B. Jemison It is certified that error appears in the above-identified patent and that said Letters Patent is hereby corrected as shown below:

Column 19, line 19 "section" should be --sections--.

Signed and Sealed this

Eleventh Day of August, 1987

Attest:

DONALD J. QUIGG

Attesting Officer

Commissioner of Patents and Trademarks